United States Patent
Wunderlich et al.

[19]

[11] Patent Number: 5,405,616
[45] Date of Patent: * Apr. 11, 1995

[54] MEANS FOR CONTAINING ACTIVE SUBSTANCES, HAVING A SHELL OF HYDROPHILIC MACROMOLECULES, ACTIVE SUBSTANCES AND PROCESS FOR PREPARATION THEREOF

[75] Inventors: Jens-Christian Wunderlich, Heidelberg; Ursula Schick, Wiesloch; Jurgen Freidenreich, Schriesheim; Jurgen Werry, Ludwigshafen, all of Germany

[73] Assignee: Alfatec Pharma GmbH, Heidelberg, Germany

[ * ] Notice: The portion of the term of this patent subsequent to Mar. 28, 2012 has been disclaimed.

[21] Appl. No.: 876,864

[22] Filed: Apr. 30, 1992

[30] Foreign Application Priority Data

Jan. 17, 1992 [DE] Germany ............... 42 01 179.5

[51] Int. Cl.⁶ ............... A61K 9/20; A61K 9/50; A61K 9/14
[52] U.S. Cl. ............... 424/451; 424/195.1; 424/456; 424/464; 424/484; 424/485; 424/486; 424/487; 424/488; 424/492; 424/520; 424/489
[58] Field of Search ............... 424/195.1, 520, 408, 424/456, 484, 485, 486, 487, 488, 492, 401, 451, 464

[56] References Cited

U.S. PATENT DOCUMENTS

| | | | |
|---|---|---|---|
| 3,691,281 | 9/1972 | Battista | 424/195.1 |
| 4,470,202 | 9/1984 | Buxton et al. | 34/5 |
| 4,892,741 | 1/1990 | Qhyn et al. | 424/479 |
| 4,895,724 | 1/1990 | Cordind et al. | 424/94.1 |
| 4,933,186 | 6/1990 | Qhyn et al. | 424/476 |
| 4,933,186 | 6/1990 | Qhyn et al. | 424/476 |
| 5,019,400 | 5/1991 | Gombotz et al. | 264/13 |
| 5,019,400 | 5/1991 | Gombotz et al. | 424/497 |
| 5,089,407 | 2/1992 | Baker et al. | 435/179 |

FOREIGN PATENT DOCUMENTS

| | | | |
|---|---|---|---|
| 0382582 | 4/1990 | European Pat. Off. | 264/13 |
| 0362582 | 11/1990 | European Pat. Off. | |
| 1293128 | 11/1989 | Japan | |
| 2160100 | 12/1985 | United Kingdom | 424/486 |
| 2160100 | 12/1985 | United Kingdom | |

*Primary Examiner*—D. Gabrielle Phelan
*Assistant Examiner*—Peter F. Kulkosky
*Attorney, Agent, or Firm*—Omri M. Behr; Matthew J. McDonald

[57] ABSTRACT

The invention is directed to exactly dosable molded particles, for example granulates or pellets comprising hydrophilic macromolecules, active materials and additionally further pharmaceutically acceptable skeleton formers and additives wherein the active substance is provided to the matrix, dissolved, suspended or emulsified and a new process for the preparation of such molded particles wherein the process is particularly economically and ecologically unburdensome, as well as the use of such molded particles as pharmaceuticals in which the bioavailability, shelf life, and acceptability ar improved. Furthermore, by means of the molded particles of the present invention, mixtures, intermediates, and end products may be provided for the fields of pharmacy, cosmetics, diagnostics, and analysis and dietetics (health care).

33 Claims, 1 Drawing Sheet

MEANS FOR CONTAINING ACTIVE SUBSTANCES, HAVING A SHELL OF HYDROPHILIC MACROMOLECULES, ACTIVE SUBSTANCES AND PROCESS FOR PREPARATION THEREOF

FIELD OF THE INVENTION

The invention concerns exactly dosable molded particles comprising hydrophilic macromolecules, active materials and if desired further pharmaceutically acceptable skeletal and inactive ingredients whereby the active substance is present in the dissolved suspended or emulsified state in the matrix, as well as a new process for the formation of such molded particles as well as its use as pharmaceutical materials, cosmetics, diagnostics or dietetic foods (health care).

BACKGROUND OF THE INVENTION

Granulates suitably pellets as molded particles serve in the pharmaceutical industry mainly as intermediate products for tableting. The molding should thus lead to a free flowing, granular and dust free product, that, because of its uniformity, improves the technological processing and dosage exactness. Furthermore, pellets have, as modern multiple unit dosage forms, for example charged to hard gelatin capsules as opposed to single unit dosage forms such as tablets or dragees, a plurality of advantages:

They are evenly distributed in the gastrointestinal tract.

Because of their small size as opposed to the monolithic dosage forms they result in shorter stomach residence times, more particularly so in gastric juice resist coated dosage forms.

They dissolve more quickly in the gastrointestinal tract as single aggregates in contrast to a compressed table which must first dissociate into its granulated portions.

Pellets with different active substance release rate can be provided in a single dose in mixed form.

Nevertheless, all processes of the state of the art have the basic problem of the need to provide form to powdery crystalline, active and inactive ingredients to utilizable granulates (pellets) as molded particles.

One must differentiate therein between associating and dissociating procedures. It is common to all processes that for a long time it has been possible to arrive at granulates suitably pellets as molded particles only via a plurality of expensive partial steps.

In the dissociative procedures, summarized in simplified form, the pharmaceutically active and inactive ingredients are diminuated through sieves to a uniform grain size and then mixed. Thereafter follows dry or damp granulation in which the powder mixture is aggregated and subsequently reduced in size to granular grains. In the next step, if necessary, there is drying and again sieving.

In associatively constructed granulates, the powder formed pharmaceuticals and inactive ingredients are formed into granulated grains in a controlled process (for example Vortex layer process) under the continual addition of a granulating fluid under the simultaneous drying.

During a subsequent, special rounding procedure (for example, Marumerizer ®) round, spherical granulate particles (pellets) are achieved. The disadvantage hereby is that in rounding out of already created, unformed granulated particles, a mass of substance containing the pharmaceutical is lost and cannot be directly recycled into the granulation process. This of course creates a expense and clean-up technological problem. At the same time mechanical forming leads to a product of uneven size.

Special pelleting techniques are for example the associative dry pelleting through compacting and the Vortex layer granulation which give very unsatisfactory results with respect to form and mechanical stability of the pellets.

All these production processes require technologically expensive multistep procedures. They are characterized by a plurality of technological process parameters, for example temperature, moisture content, homogeneity of the mixtures and so on.

Furthermore, in all granulation and pelleting procedures the provision of a whole row of inactive ingredients is required. Thus, for example, binding materials or granulating fluids must be provided in order to bring the powdery substrate into a solid compact and workable form. Most knowledge is required about the physico-chemical conditions, for example heat of solution, solubility or crystal formation tendency and considerable experience in utilizing these materials is necessary in order to be able to judge the coworking of these additive materials with each other and with the pharmaceutically active substance in conjunction with all of the process parameters.

Thus, the pharmaceutical requirements for a granulate (pellets) are often only fulfilled by empirical experiments in dependence upon the pharmaceutically active material to be processed and the dosage form to be formulated therefrom.

It is thus understandable that the maintenance of constant production requirements in these complex processes is very difficult. Thus, it is because the plurality of parameters which must be considered in the known production processes, and despite high development and optimization expenditures, it is not possible to find a suitable process for every pharmaceutically active material.

When one considers the pellets or granulates formed in accordance with the state of the art and furthermore the biopharmaceutical aspects thereof, so it must be recognized that the pharmaceutically active materials of these aggregated molded bodies are only available to the organism after disaggretation and subsequent release. The plurality of substantially distinguishable holding and binding forces in granulates clarifies this problem. Because of the utilization of hardening binders in the drying step (damp granulation) or via sintering or melt-binding under the influence of pressure (dry granulation), solid are formed, whose binding forces must be overcome in the organism in order for the pharmaceutical material even to be released in active form.

Every production step in the process of the state of the art can act as an undesirable influence on the release of the active substance and thus its bioavailability.

The present invention thus has the task to suggest new molded particles, a process for their preparation as well as mixtures, which, on the grounds of their structure and composition improve the bioavailability and compatibility of the active substances, are shelf stable, exactly dosable, providable as single or multiple unit doses and are ecologically compatible, and can be produced in a simple and economical manner. In such a way that the active materials are processed in a protected way and thus the disadvantages of the state of the art overcome.

SUMMARY OF THE INVENTION

The problem is solved by the invention by the provision of active substance containing molded particles which are characterized thereby that the pharmaceutically active material is provided in dissolved, emulsified, or suspended form in a solid or semi-solid matrix which comprises principally, as skeleton former, hydrophilic macromolecules of natural origin.

As hydrophilic macromolecules there may be utilized collagen, gelatin, fractionated gelatin, collagen hydrolysates, gelatin derivatives, plant proteins, plant protein hydrolysates, elastin hydrolysates and combinations of the foregoing materials with each other.

In particular, the present invention makes available molded particles containing active substances which are characterized by a dispersion of at least one active substance or mixture of active substances in a matrix which comprises principally a skeleton builder of hydrophilic macromolecules which are selected from the group consisting of collagen, gelatin, fractionated gelatin, collagen hydrolysates, gelatin derivatives, plant proteins, plant protein hydrolysates, elastin hydrolysates and mixtures of the above identified materials.

This task is further solved by the provision of a procedure for the production of molded particles containing an active substance characterized thereby that the active substance is dissolved, emulsified or suspended in a solution of the hydrophilic macromolecule (skeleton builder).

If desired, the molded particles may be dried.

In particular, the present invention provides a procedure for the formation of molded particles containing at least one active substance characterized thereby that:

a) a skeleton builder of hydrophilic macromolecules selected from the group consisting of:

collagen, gelatin, fractionated gelatin, collagen hydrolysates, gelatin derivatives, plant proteins, plant protein hydrolysates, elastin hydrolysates is mixed with the active substance, and b) the thus obtained mixture of skeleton builder and dispersed active substance is dropped into an exceedingly cold fluid and the molded particles thus formed.

As molded particles in the sense of the present invention as it is understood are those selected from the group consisting of powders, granulates, and pellets in substantially symmetrically formed aggregates.

In accordance with the present invention unitary round molded particles in particular pellets, are particularly suited for pharmaceutical uses wherein the concept of pellet comprises a grain size of between 0.2 to 12 mm.

In the description of the invention the properties, production, and use of round pellets are preferentially disclosed.

Nevertheless, one skilled in the art can provide other molded particles selected from the group consisting of powders, granulates, in substantially symmetrically formed aggregates, advantageously for the formation, in particular, of dosage forms.

Furthermore, the task of the present invention is solved by a mixture which comprises at least one active substance and one skeleton builder characterized thereby that the skeleton builder is a hydrophilic molecule selected from the group consisting of collagen, gelatin, fractionated gelatin, gelatin derivatives, collagen hydrolysates, plant proteins, plant protein hydrolysates, elastin hydrolysates, albumins, agar agar, gum arabic, pectin, tragacanth, xanthan, natural as well as modified starches, dextrans, dextrins, maltodextrin, chitosan, alginates, cellulose derivatives, polyvinyl alcohol, polyvinyl pyrrolidone, polyacrylic acid, and polymers of methacrylic acid and methacrylic acid esters, as well as mixtures thereof.

The preferred embodiments of the invention are described and claimed in the subclaims.

The solid to semi-solid or gel formed pellets of the present invention are spherical, unitary, molded particles in the range of 0.2 to 12 mm. Pellets in the range of 0.2 to 2 mm are suitable for multiple unit dosage forms, pellets in the range of 2 to 12 mm. are usable as single unit dosage forms, In order to provide certainty with respect to pharmaceutically active materials, the pharmaceutical industry is required to provide the appropriate dosage forms which have dosage exactness, homogeneity, compatibility, and satisfactory shelf life. In conventional production of pharmaceuticals, this standard can only be reached with high and capital intensive expenditures. The unitary grain size distribution of the claimed pellets combined with a homogeneous distribution of the active substance substantially improve the dosage exactness with respect to the state of the art. Furthermore, the active substances embedded in the pellet matrix can be brought into a shelf stable form which has a high level of mechanical stability with a very low friability. Sensitive active substances are thus reliably shielded from external influences.

The pellets of the present invention which are molded particles which are characterized by their unitary round and even state are, because of their harmonious general impression are highly optically appealing and can improve their acceptance by the patient. By the appropriate coloration, the clear, transparent, and shiny, opaque through transparent or non-transparent appearing particles, can be developed to form non-confusable medicinal specialties.

Through the advantageous colloid protective function of the appropriate macromolecule and the simultaneous embedding of the active substance in the polymeric matrix skeleton, the toleration of, in particular, mucosally irritating substances, can be substantially increased. The dosage forms described herein are pleasant tasting and are readily administered perorally.

It is the surprising finding of this invention that with all pharmaceutical materials, irrespective of whether they are dissolved, suspended, or emulsified in the pellets of this invention which exist as molded particles, in contrast to the conventional granulates, pellets or tablets, the liberation of the active substance in the organism proceeds without a previous disassociation procedure. In conventional preparations it was first necessary that the holding and binding forces which make possible a formed dosage format be overcome. Furthermore, the thus obtained subaggregates have to be cross-linked and dissolved till the pharmaceutical material is finally in an absorption capable format. Conventional solid dosage forms depending on the inactive ingredients utilized, as well as the production procedures employed, can substantially reduce the bioavailability of the active substances.

The mode of solution of the dosage form as a time dependent factor with respect to the pellets of the present invention as molded particles depends solely on the type and composition of the hydrophilic matrix system and thus, is modulatable with respect to the release rate. Thus, acute forms which dissolve in a few seconds can also be formulated as sustained release doses. The solution of the skeleton former is the rate determining step.

With hydrophobic or pharmaceutical substances which have low solubility, the described hydrophilic macromolecules improve the absorption, that is to say, the bioavailability and can be adjusted to the appropriate physicochemical and pharmaceutical properties of the appropriate active substance.

Active substance containing pellets are held at low temperatures during the protective production process (provision of form) and only come into contact with an inert medium (liquid nitrogen). This avoids any change in the pharmaceutical material or contamination with residual cooling oil such as organic solvents as is known with the classical soft gelatin capsule process.

Under the heading of technological and biopharmaceutical aspects, the described pellets fulfill all the principle requirements which are placed upon such a dosage form, namely:

They are constant in form and color.
They possess a grain size within a narrow range.
They are easily dosable and fillable.
They have a high degree of mechanical stability and shelf life.
They release the active substance either rapidly or in a controlled manner.

In the sense of the invention, alone or in mixtures, hydrophilic macromolecules may be utilized which are selected from the group consisting of collagen, gelatin, fractionated gelatin, gelatin derivatives, collagen hydrolysates, plant proteins, plant protein hydrolysates, elastin hydrolysates.

These biogenic materials create no pharmaceutical problems and are non-toxic. The matrix properties of the named protelnaceous material are utilizable within wide parameters depending upon the exact knowledge of their physicochemical properties and lead to dosage form in which the desired active substance is present in an optimal and reproducible manner.

Gelatin is a collagen containing material derived from sclero protein which, in accordance with the mode of preparation, has different properties. It exists substantially of four molecular weight fractions which influence the physicochemical properties in dependence upon the molecular weight and percentage proportion. The higher for example the proportion of microgel ($10^7$ to $10^8$ D), the higher is also the viscosity of the aqueous solution. Commercially available materials have up to 10%. The fraction of alpha gelatin and its oligomers ($9.5 \times 10^4/10^5$ through $10^6$ D) are determinative for the gel solidity and generally constitutes between 10 and 40 wt. %. Molecular weights under that of alpha gelatin are designated as peptides and in conventional gelatin qualities (low bloom) can constitute up to 80 wt. %.

Gelatin has a temperature and concentration dependent reversible sol/gel transformation property, which is dependent upon the molecular composition. The measure of the gel formation property of the gelatin is, in international usage, designated as the bloom number. Lower levels of commercial qualities begin at 50 bloom, high bloom varieties have a level of about 300 bloom.

The chemical and physical properties vary in accordance with the mode of preparation wherein particularly protective isolated gelatin types (low proportion of dextrorotatory amino acids and peptides have a short sol gel transformation rates and melting points above 37° C., measured as a 10% solution.

Fractionated gelatins are a special type of gelatin and are obtained by special production techniques for example ultrafiltration from conventional gelatin. The composition can be varied for example by the removal of peptides (molecular weight less than $9.5 \times 10^4$ D) or by mixtures of individual fractions such as for example alpha chains, dimers and timer chains or microgels.

Furthermore, gelatin for example fractionated gelatin, has good tenside properties with protective colloidal action and emulsifying ability.

Collagen in native form is water insoluble. Through special production modes it is possible to obtain collagen types which are soluble having an average molecular weight of about 300,000 D.

Gelatin derivates are chemically altered gelatins for example succinylate gelatin which, for example, can be used as a plasma expander.

Under the term collagen hydrolysate there is understood a product obtained from collagen or gelatin by pressure or enzymatic hydrolysis, which no longer has the sol/gel transformation ability. Collagen hydrolysates are readily cold water soluble and the molecular weight composition may lie between a few hundred D and below $9.5 \times 10^4$ D. The substances obtained by the enzymatic method are more homogeneous in their molecular composition and still show good tenside and emulsifying properties.

Newly developed products are those from plant proteins and the hydrolysates thereof which correspond to a very large extent in their properties to those of collagen hydrolysates. They are preferably obtained from wheat and soya and have molecular weight ranges of 200,000 to 300,000 D and from about 1,000 to about 10,000 D respectively.

Elastin hydrolysates are obtained enzymatically from elastin and consist of a single peptide chain. Because of their high proportion of non-polar amino acids these can be utilized in lipophilic systems. Elastin hydrolysate has a molecular weight in the range of about 2000 to 3000 D and readily form films on the skin.

In the use of plant proteins, plant protein hydrolysates, elastin hydrolysates for example those obtained from collagen hydrolysates (cold water soluble gelatins or gelatins with a maximum molecular weight distribution from a few hundred D to below $10^5$ D (Variant A) the carrier material forms the desired molded particle. In a preferred embodiment of the present invention, lyophilization surprisingly yields a highly porous and at the same time mechanically stable matrix which is rapidly and totally soluble in cold water.

Where the pharmaceutical material is present in the matrix in a dissolved or suspended form, all of the hereinabove recited hydrophilic macromolecules which lie in the indicated molecular weight range may be utilized either by themselves or in mixtures. Emulsified pharmaceuticals with rapid release are advantageously produced by the use of collagen hydrolysates which still have tenside and emulsifying properties. Particularly advantageous are the enzyme produced hydrolysates which have a molecular weight of between about 15,000 to 20,000 D.

The rapid solution of the described matrix prescriptions are suitable for rapid release dosage forms in which the active substance is present in single or multiple doses.

For internal consumption, pellets in the form of molded particles advantageously be used for instant formulations. Where, for example the active material is embedded in a very rapidly dissolvable matrix and pelleted, there are obtained shelf stable pellets which (for example when charged to bags) can be entirely dissolved in cold water in the space of a few seconds.

In accordance with the present invention hydrophilic macromolecules with sol gel forming properties, such as for example gelatin and fractionated gelatin whose maximum molecular weight distribution is above $10^5$ D, may be utilized as skeleton substances.

Where, on the other hand, the active substance in dissolved, suspended or emulsified form, is present in a sol/gel forming skeleton matrix (Variant B) utilizing gelatin or fractionated gelatin, one obtains pellets which, depending upon the molecular composition of the utilized gelatin types, will dissolve slowly or rapidly in aqueous medium at 37° C.

In a further embodiment of the invention, softening agents may be added in the range of 1 to 50% (relative to the entire worked mass) selected from the group consisting glycerol, propylene glycol, polyethylene glycols, triacetin, sorbitol, sorbitan mixtures, sorbitol solution, glucose syrup and other polyols such as sugar alcohols. The named materials influence the consistency of the matrix of the present invention to provide a range property from solid to semi-solid or gel forming, its solubility and the viscosity. It is particularly advantageous to use sorbitol as the softening agent since its quality as a non-cariogenic sweetener simultaneously serves as a taste adjuster.

In a particular embodiment of the invention, pellets from matrix masses having softener additives in the range of 20–50% (relative to the entire working mass) have distinct bioadhesive properties.

For pellets as molded particles which are soluble in water at 37° within as few minutes, it is preferred to utilize types of gelatin whose peptide proportion is above 30% and which have a maximum molecular weight range of between about $10^5$ D to $10^6$ D.

For the formulation of sustained release properties in the purview of the present invention, it is desirable to utilize gelatin types with a peptide proportion of less than 10% and a microgel proportion of 20–15%. Thus constructed matrixes in particular mixtures having a melting range in an aqueous medium, of between 35° C. to 40° C. suitably above 37° C. There may be added softening agent in the range of 1 to 30% (relative to the entire working mass).

As additional skeleton builders in the range of 1 to 50% (relative to the entire working mass) there may also be added albumins, agar agar, gum arabic, pectins, traganth, xanthan, natural as well as modified starches, dextrans, dextrins, maltodextrin, chitosin, alginates, alginate calcium phosphate, cellulose derivatives, polyvinyl alcohol, polyvinyl pyrrolidone, polyacrylic acid, and polymers of methacrylic acid and methacrylic acid esters.

In a further embodiment of the invention there may be added between 1 and 50% additives of materials selected from this group in order to adjust certain physical and chemical properties of the matrix such as viscosity, mechanical stability or solubility properties of the polymeric skeleton with respect to the active material and the particular use selected. Thus, for example materials such as dextrans, modified starches, sugar and in particular, mannitol containing pellets, are formed which, as lipophilisates form a high porous network. Macromolecules such as alginates, agar agar, and pectin can be utilized to provide further delay or modification of the release of the active substance.

To this basic mass, pharmaceutically acceptable inactive ingredient and carrier materials may be added, for example, fillers such as lactose, dispersing agents such as disodium phosphate, pH adjusters such as disodium citrate, emulsifiers such as lecithin, stabilizers such as ascorbic acid, cosolvents such as polyethylene glycol, natural colorants for example carotinolds, odorants or flavorants for example sugar replacement materials, complex formers or chelating agents for example cyclodextrins.

In a particular modification, the matrix mass set forth in Variant A and B, for example mixtures, which can be constructed with or without the addition of softening agents, there may be added gastric juice resistant materials selected from the group consisting of poly and methacrylic acid derivatives, cellulose derivatives and mixtures thereof to form pellets wherein the active material is released solely after passage through the stomach, that is to say, that the skeleton former of the matrix mixture is dissolved in a predetermined pH range.

In the case of alginate containing base receptors by suspension of water insoluble dicalcium hydrogen phosphate, $[(Ca_2(HPO_4)_2]$ for example in a pH neutral or slightly basic gelatin/alginate mixture, it is possible to produce pellets which delay release of the active substance. During the passage through the stomach, the acid medium dissolves the calcium salt and cross-links the alginate. In a further embodiment utilizing collagen derived skeleton materials, pharmaceutically acceptable hardening agents such as aldoses or citral may be added, which after drying, lead to cross-linking. Pellets formed in this manner no longer dissolve in aqueous medium.

Since the pellets of the present invention, as molded particles, have high mechanical stability, they can be coated with pharmaceutically acceptable film formers. It is particularly advantageous to combine matrix masses which have special bioadhesive properties with film coatings (for example poly and methacrylic acid derivatives) which dissolve in defined pH ranges which are directed to achieve the desired absorption segment in the gastrointestinal tract. These methods of proceeding make it possible to bring pharmaceutical materials with problematic bioavailability into controlled absorption. Furthermore, through combination with film formers, pellet mixtures in accordance with the present invention may be produced which release the active material in a pulsed manner.

It is well known that gelatin, in accordance with the mode of production, has an isoelectric point in the acid (type B gelatin) or alkaline type A gelatin range. This property may be utilized for the direct formation of micro or nanno capsules in the matrix mass. Thus the use of gelatins with opposing charge in the mixture with an active substance containing solution (for example at pH of 6 to 7), the desired macrocapsules are produced, by removal of the solvent. By utilization of gelatin types in collagen derivatives with a defined molecular content, it is possible to form 3-dimensional networks in the nannometer range. Gelatins or collagen hydrolysates can furthermore form conjugates with the active materials by the addition of approximately 2 to 3% addition of salts.

In accordance with the present invention, active substances with problematic bioavailability can be provided in a further embodiment by the direct and controlled precipitation of the active substance previously dissolved in the matrix mass, for example by pH shifting or removal of the solvent, to provide a finely dispersed absorption accelerating form.

Pharmaceutically acceptable organic solvents and cosolvents which are preferably miscible with a aqueous solution can be added to the claimed matrix masses, where the active substance is water insoluble.

Hereinbelow a process for the preparation of the pellets of the present invention will be described in further detail.

Further embodiments of the present invention are set forth in the United States application for Letters Patent as set forth herein, whose disclosure is incorporated herein by reference. These parallel U.S. applications have been filed in the United States Patent and Trademark Office by the same inventors on the same day and are as follows:

Title: "Aloe Vera Juice Containing Pellets for Production Thereof and the Use Thereof as Pharmaceutical Cosmetic and Peroral Agents", U.S. Ser. No. 07/876,876.

Title: "Pellets Containing Peptides, Method of Making Same and Use Thereof", U.S. Ser. No. 07/876,865.

Title: "Pellets Containing Plant Extracts, Process of Making Same and Their Pharmaceutical Peroral or Cosmetic Use", U.S. Ser. No. 07/876,866.

Title: "Soft Gelatin Capsules", U.S. Ser. No. 07/876,863.

Title: "Peroral Dosage Form for Peptide Containing Medicaments, in Particular Insulin", U.S. Ser. No. 07/876,867.

Title: "Pellets Containing Dihydropyridine Derivatives Process for Production Thereof and Use as Rapid Action Dosage in Heart and Circulatory Diseases", U.S. Ser. No. 07/876,877.

In the simplest case, the process of the present invention for the formation of active substance containing molded particles can be described in the following two process steps:

a) The active substance is mixed with a skeleton former of hydrophilic molecules.

b) The thus obtained mixture comprising the skeleton former and the dispersed active substance is dropped into an exceedingly cold fluid whereby the molded particle is created.

In one mode of procedure the process step described in (a) above, there is created a mass capable of forming drops comprising substantially hydrophilic macromolecules as skeleton builders, in particular plant proteins, plant protein hydrolysates, coilsgert, gelatin, fractionated gelatin, elastin hydrolysate, collagen hydrolysates, gelatin derivatives, or mixtures of the above-named materials, together with the active substance.

Thereafter, the active substance is dispersed, that is to say, dissolved, suspended or emulsified, in the above-identified skeleton former, in particular, plant proteins, plant protein hydrolysates, collagen, gelatin, fractionated gelatin, gelatin derivatives, collagen hydrolysates, or elastin hydrolysates, wherein the type and amount of the utilized skeleton former and similarly the incorporation therewith of former additives depends upon the ultimate desired use of the molded particles.

A concentration of the carrier material can, for example, vary between 0.5 and 60% (w/w) suitably 0.5 to 30%, (based upon total working mass). The use of warming in the temperature range of about 30° C. to 60° C., suitably about 45° C. can, for example, where gelatin is used, be helpful in order to convert this into the sol form.

There may also be added to the matrix mass, additional skeleton formers in the range 1–50% (relative to the total work mass) selected from the group consisting of albumins, agar agar, gum arabic, pectin, traganth, xanthan, natural as well as modified starches, dextrans, dextrins, maltodextrin, chitosin, alginates, alginate calcium phosphate, cellulose derivatives, polyvinyl alcohol, polyvinylpyrrolidone, polyacrylic acid, and polymers of methacrylic acid and methacrylic acid esters.

In a further process variation there may be provided to the matrix, amounts of softening agents from 1° to 50° C. (based upon the total mass to be worked) selected from the group consisting of glycerol, propylene glycol, polyethylene glycol, triacetin, sorbitol, sorbitan mixtures, sorbitol solutions, glucose syrup and other polyols, for example, sugar alcohols.

To this base mass, there may added pharmaceutically acceptable inactive ingredients and carrier materials for example, fillers such as lactose, dispersants such as disodium hydrophosphate, pH adjusters such as disodium citrate, emulsifiers such as lecithin, stabilizers such as ascorbic acid, cosolvents such as polyethylene glycol, natural colorants for example carotinolds, odorants and flavorants for example sugar substitutes, complexing agents or chelating agents for example cyclodextran.

Clearly, the mixtures of the present Invention may be utilized for immediate processing in fluid form for completion in containers, for example molds and soft gelatin capsules as well as other encapsulations.

In another embodiment, the process step described as b) provides that the described matrix mass is dropped into a dropping bath in the range of −70° C. to about −270° C., suitably from about −100° to about −220° C. to provide the spherical shape (molding) and shock freezing. As the exceedingly cold suitably inert fluid there is preferably used liquid nitrogen which does not alter the components of the pellets. In the exceedingly cold fluid such round molded particles (pellets) are formed, which after drying, have an exceedingly mechanically stable matrix. The molding is achieved via an appropriate dosing system. Every discrete drop thus takes on its spherical shape either already in free fall or on the other hand, in the dropping bath by the action of the surrounding gas capsule, that is to say, the surface tension of the system/gas interface, before a total freezing takes place. Just this rapid but yet graduated controllable freezing fixes the desired condition of the system instantaneously, that is to say, no active substance can diffuse into the surrounding medium, dissolved segments can no longer crystallize out, suspensions can no longer sediment, emulsions can no longer break down, thermally sensitive or moisture sensitive active substances are cryoconserved, the carrier skeleton can no longer shrink and so on. The production process utilizing inert fluid gas thus has no negative impact upon or change of either the active substance nor the matrix mass. In a particular advantage that one thus obtains the desired properties. Furthermore, as the process operates in an absence of solvent, there is no negative environmental impact and it can be carried out under sterile conditions.

Any procedure may be used as the dosage system which yields a discrete even product, that is to say, drops of predetermined size.

If one utilizes an uncontrolled dropping arrangement, there is provided a granulate. By utilizing a suitable spray or dust jet with a dosage pump, the molded particles are obtained suitably as powder.

Furthermore, there may be used in the process, dosage arrangements equipped with jets which expel the dropping material in a timed or intermittent manner.

In a further preferred embodiment of a process of the present invention, there is utilized the procedure developed by Messer Griesheim GmbH designated Cryopel ® (based upon DE OS 37 11 169). In combination with a dip freeze arrangement, the Cryopel ® arrangement makes the conversion of the process of the present invention to an industrial scale particularly easy. This arrangement, which can be operated with liquid nitrogen, has been found to be particularly economical. This arrangement is also suitable for the production of sterile materials. Continuous work modes with a little maintenance or cleaning expenditure makes possible the economic conversion of the process of the present invention into the industrial scale.

Figure 1:
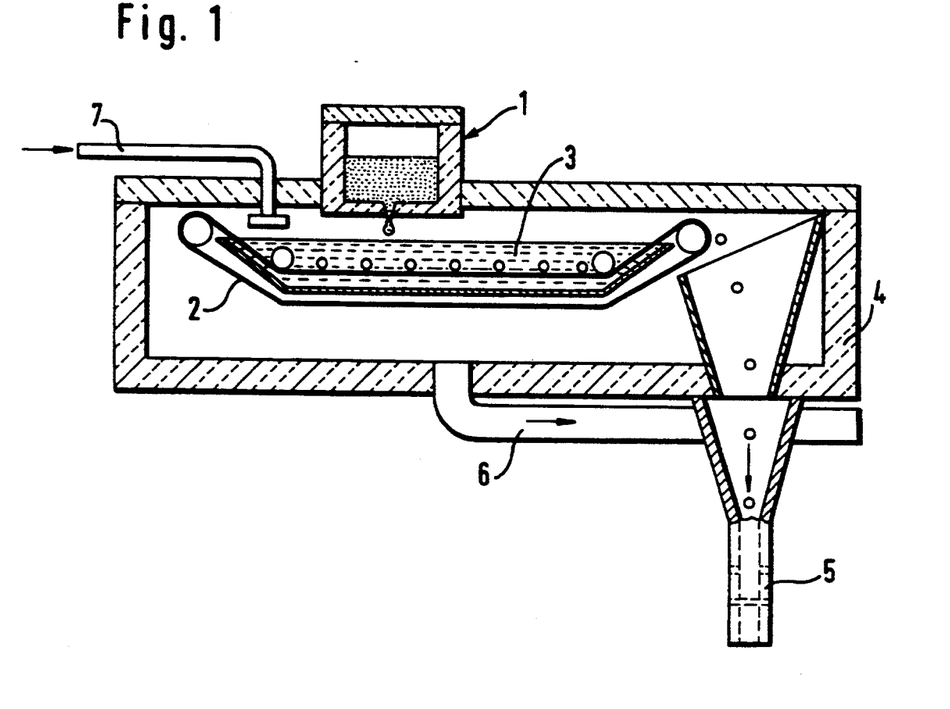
FIG. 1 is a schematic representation in cross-sectional elevation of an arrangement for carrying out the process of the present invention.

FIG. 1 is a schematic representation of the Cryopel ® process developed by Messer Greisheim GmbH. The matrix mass of the present invention is dropped via calibrated jets into the fluid nitrogen bath 3 held at −196° C. whereby under simultaneous shock freezing they are converted into round pellets. Via the continuously running transport band 2, frozen product is removed via arrangement 5. The dosing of the liquid nitrogen is carried out via line 7 and the thus produced nitrogen is removed via line 6. The insulation 4 surrounds the entire system.

Figure 2:
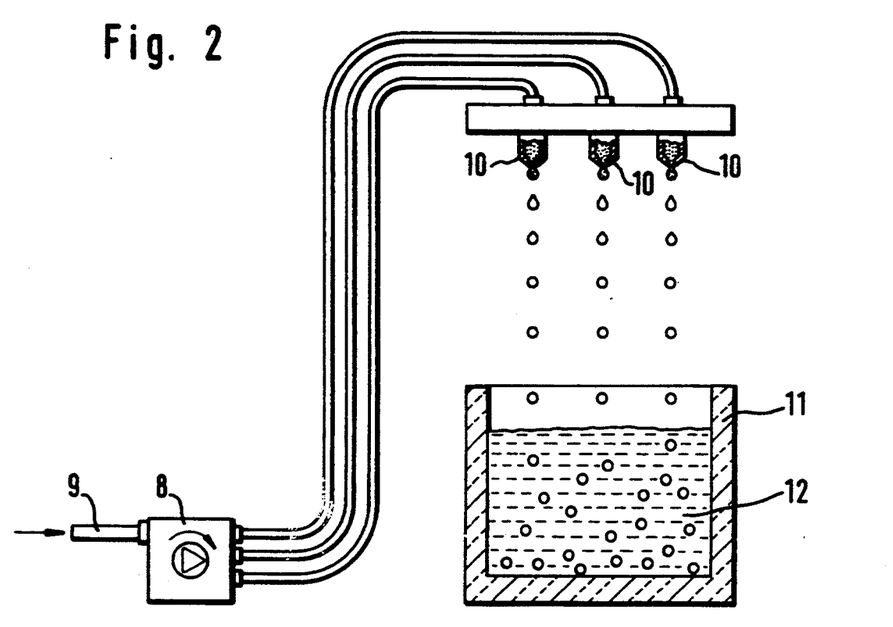
FIG. 2 is a further arrangement for carrying out the process of the present invention in schematic representation.

In FIG. 2 there is shown a schematic representation of the process wherein, via a controllable dosage pump 8, the cold or up to maximum of 60° warmed matrix is continually lead via line 9 to heat dropping jet 10 to be dropped into the insulated bath 11 containing liquid nitrogen. The shock formed pellets are removed batchwise. With this arrangement is possible to operate with highly viscous masses.

Where the system to be processed is not sufficiently capable of flowing or forming drops, one can, for example, add additional amounts of water of between 1 and 10 wt. %, the processing temperature may be raised or pressure may be utilized in the dosage step. In the contrary case, for example the system has too low a viscosity, analogously, reduced pressure may be utilized. This mode of proceeding provides a regular formation, as well as separation, of individual drops.

The processing temperature may be varied across a wide range. However where thermally sensitive peptide pharmaceuticals are utilized, this should lie under 50° C.

Thus, for example utilizing the Cryopel ® dosing arrangement, substances in the viscosity area of $1 \times 10^{-3}$ to 12.5 Pa seconds can be dosed without any difficulty.

Additional very cold fluids which may be utilized for the process of the present invention include for example, liquid inert gases, for example argon.

In dependence upon the dosage system chosen, a grain size compatibility of over 80% can be achieved which can be increased through classification.

The material separated through classification can again be converted into the fluid state and repelletized so that a waste free procedure is yielded.

In one embodiment of the described process step the pellets are dried wherein two process variations are provided.

Variant A

The molded particles, i.e., pellets frozen at −196° C. are transferred into a freeze drying arrangement. There are chosen temperatures of about 15° C. below the sublimation point of water at a pressure of 0.1 Pa to 103 Pa (0.001 to 1.03 mbar). The drying process which is carried out in a conventional freeze drying apparatus (condenser temperature −40° C.) at a temperature of 25° C. and 33 Pa (0.33 mbar) proceeds in the primary drying step in the sublimation out of the matrix of the water amorphously frozen in the shock freezing, the secondary drying (desorption) leads to an end product with a highly porous network. Shock freezing prevents the conversion of the water into crystalline form whereby there is provided a solid finely dispersed amorphous water phase in the matrix. After sublimation of the thus existing water, there are formed highly porous micropore containing networks which have a substantially higher surface area than those obtained by the conventional freeze dried procedures. Such pellets are, compared to conventionally freeze dried products, particularly readily soluble and are preferred for the development of instant preparations.

Variant B

The frozen molded particles, i.e., pellets are permitted to thaw and are conventionally dried. Here, it is advantageous for the acceleration of the drying process and the maintenance of a low temperature, to operate under vacuum, 3000 to 5000 Pa (30 to 50 mBar). Drying temperatures of up to 50° C. may be chosen, whereas the temperature in the pellet matrix during the drying stage of pellet matrix, because of the evaporation enthalpy of the fluid does not raise above 30° C.

For conventionally dried pellets (Variant B) it is necessary to utilize sol/gel forming substances for the matrix which are capable of forming drops in sol form and, after cryopelletization and the thawing forma gel, which is stable after drying. The provision of softening agents influences the matrix mass with respect to consistency. The thus produced pellets are characterized by a particularly economical mode of production since the process step of lyophilization is not absolutely necessary.

It is particularly advantageous to carry out the process without the addition of further lipophilic emulsifying materials, for example utilizing ultrasound homogenizers where there are utilized gelatin types and collagen hydrolysates with higher molecular weights, before the further processing into stable emulsions, that is to say, microemulsions.

Lipophilic/oily substances can for example be garlic oil, cod liver oil, Vitamin E and other non-fatty vitamins, St. Johns's Wart Oil, lecithin, juniper Oil, Omega-3-fatty acids, primrose Oil, etheric oils, etc. With plant extracts whose active components have hydrophilic as well as lipophilic properties, the lipophilic portion is first emulsified in the matrix and the water soluble portion is dissolved in a hydrophilic matrix mass and subsequently cryopelletized.

Because of the high viscosity of the matrix system, active materials which are suspended can be prevented from sedimentation by simple stirring and those evenly dosed. Temperature sensitive pharmaceuticals are advantageously lyophilized.

The processing of the particular embodiments of the invention claimed in the subclaims such as formulations with controlled release, suitably absorption improvement, micro and nanoencapsulation, precipitation, conjugate formation, film coating and the coating of pellets with bioadhesive properties logically follows the description and the nature of the appropriate active substance.

The process of the present invention is, with respect to the state of the art, seen to be substantially maintenance free and can be economically carried out. The basically simple process of cryopelleting makes it possible, in a surprising manner to make substantial improvements over the state of the art.

Because of the very substantial breadth of variations of the invention, all pharmaceutical materials can be contained in the described matrix masses insofar as there is no incompatibility with the individual portions of the prescription mass. The concept of the term "pharmaceutically active substance" as considered in the present invention, can thus be defined as follows.

Pharmaceutically active substances can be synthetic or of natural origin. They may be single chemical substances or mixtures of substances as well as combinations of various pharmacologically active components. Further, the concept of pharmaceutically active material shall Include phyto-pharmaceuticals and plant extracts as well as including hormones, vitamins and enzymes.

Furthermore, enantiomer-free substances or pseudo-recemates are suitable for the present invention.

Active substances from the field of dietetic foods (health care) as well as in the field of cosmetics may be utilized.

There is no limitation whatsoever for the types of pharmaceutically active materials which can be utilized in the present invention with respect to indication groups. There follows, a generic listing of Indication groups, as well as certain species within said groups.

1. Strong analgetics, for example, i.e., morphine, dextropropoxyphen, pentazocine, pethidine, buprenorphin;
2. Antirheumatics/antiphlogistics (NSAR), for example, i.e., indomethacin, diclofenac, naproxen, ketoprofen, ibuprofen, flurbiprofen, acetylsalicylic acid, oxicame;
3. Beta-sympathicolytics, for example, i.e., propanolol, alprenolol, atenolol, bupranolol, salbutanol;
4. Steroid hormones, for example, i.e., beta methasone, dexamethasone, methylprednisolone, ethinylestradiol, medroxyprogesterone, prednisone, prednisolone;
5. Tranquilizers, for example, i.e., oxazepam, diazepam, lorazepam;
6. Alpha-sympathicolytics, for example, i.e., ergotamine, dihydroergotamine, dihydroergotoxin;
7. Hypnotics and sedatives, for example, i.e., secbutabarbital, secobarbital, pentobarbital, doxylamine, diphenyldramin;
8. Tricyclic antidepressives, for example, i.e., imipramine, nortriptyline, clomipramin, amitriptyline;
9. Neuroliptics, for example, i,e., chloroprothixen, chloropromazine, haloperidol, triflupromazine;
10. Gout material, for example, i.e., benzbromaron, allopurinol;
11. Antiparkinson materials, for example, i.e., levodopa, amantadine;
12. Coronary arterial therapeutics or calcium angatonists, for example, i.e., nifedipin, dihydropyridine derivatives, nitric esters, such as glycerintrinitrate, isosorbidomononitrat and isosorbiddinitrate; verapamil, gallopamil, molsidomin;
13. Antihypertensives, for example, i.e., clonidin, methyldopa, dihydrazine, diazoxide;
14. Diuretics, for example, i.e., mefruside, hydroxchlorothiazide, furosemide, triamterene, spironolactone;
15. Oral antidiabetics, for example, i.e., tolbutamide, glibenclamid;
16. Chemotherapeutics or antibiotics, for example, i.e., penicillin, such as phenoxymethylpenicillin, amoxycillin, ampiclllin, pivampicillin, bacampicillin, dicloxacillin, flucloxacillin, cephalosporin, such as cefalexin, cefaclor, gyrase blockers, such as nalidixic acid, oflaxacin, norfloxacin, erythromycin, lincomycin, tetracycline, doxycycline, trimethoprim, sulfamethoxazol, chloramphenicol, ribampicin;
17. Local anesthetics, for example, i.e., benzocaine;
18. ACE blockers, for example, i.e., enalapril, captopril;
19. Mucolytics, for example, i.e., acetylcystein, abroxol, bromhexin;
20. Antiasthmatics, for example, i.e., theophylline;
21. Mineral preparations, for example, i.e., magnesium-, calcium, potassium salts, iron preparations;
22. Neurotropics, for example, i.e., piracetam;
23. Antiulcer agents, for example, i.e., cimetidin, pirenzepin;
24. Protovitamins and vitamines, for example, i.e., biotin, cyanocobalamin, ergocalciferol, ascorbic acid, thiamine, pyridoxine, alpha-tocopherol, retinol, beta-carotin;
25. Peptide pharmaceuticals, for example, i.e., insulin, interferon;
26. Digitalis glycosides, for example, i.e., digitoxin, digoxin;
27. Anti emetics, for example, i.e., metoclopyramid;
28. Enzymes, for example, i.e., plasmin, desoxiribonuclease;
29. Anti-arrhytmics, for example, i.e., prajmalin;
30. Anti-epileptics, for example, i.e,, phenytoin;
31. Anti-coagulantis, for example, i.e., phenprocoumon;
32. Spasmolytics; for example, i,e., papaverine;
33. Anti-mycotics, for example, i.e., clotrimazol;
34. Hormones, for example, i.e., calcitonin;
35. Venin therapeutics, for example, i.e., aesin;
36. Immuno suppresives, for example, i.e., cyclosporin;
37. Tuberculostatics, for example, i.e., rifampicin;
38. Virustatics; for example, i.e., aminoadamantane;
39. Cytostatics, for example, i.e,, methotrexate;
40. Vaccines, for example, i.e, live polio myelitis vaccine;
41. Phytopharmaceuticals, for example, i.e., ginkgo biloba extract;

42. Materials for the treatment of AIDS, for example, i.e., renin antagonists.

With respect to the state of the art, in the procedures of the present invention are particularly advantageous in permitting the processing (to dosage forms) of active substances with poor stability or problematic bioavailability such as light, oxidation, hydrolysis, and temperature sensitive materials, such as for example substantially insoluble pharmaceuticals, peptides, natural products enzymes, vitamins, etc.

The utilization of the powders, granulates or pellets of the present invention as molded particles can proceed, for example via a conventional dosage system in hard gelatin capsules or as a granulate in bags. Because of the good sprinkleability, that is to say, substantially round form of the granulate, it is possible to achieve good dosability. In the use of pellets there is achieved the most compact spherical packing in exact determination of the discharge volume of the capsule size (possible). Furthermore an improvement in the dosage exactness results in the fillings thereof. Beyond this by selecting the appropriate pellet size, it is possible to avoid the use of adding filler materials.

The pellets of size of between 2 and 12 mm. can, in accordance with the invention, be utilized for a new single dose buccal, nasal, or peroral dosage form. Perorally introduced pellets are readily swollowable and can readily be dispensed in an environmentally acceptable way in glasses with dosage dispensers. In buccal and nasal use, there may be utilized such molded particle/pellets with bioadhesive qualities.

Powders, granulates, or pellets, as molded particles, from matrix masses which dissolve rapidly and completely in water, can be utilized, when dispensed in bags, as instant preparations for the pharmaceutical or dietetic area (health care).

Surprisingly by utilization of the bioadhesive property of the sol gel formers in particular gelatins, in molded articles of the present invention, may be used in buccal and nasal formulations, that is to say, dosage forms with pH controlled release.

A further use of these special granulates or pellets as molded particles is provided through their direct compressibility to tablets. The thus obtained tablets show, with low friability and high breakage resistance, a surprisingly complete dissolution in less than 5 minutes, suitably 2 minutes as measured by conventional test methods (for example dissolution test apparatus as specified in the U.S. Pharmacopeia). Surprisingly, the good solubility properties of the skeleton matrix still remain after compression. The tablets dissolve directly without extended dissociation. In contrast thereto, tablets compressed from conventional granulates who was first dissociate into granular particles and merely then do they dissolve.

Formation of tablets from freeze dried molded particles of the present invention is for example, of importance in the formulation of dosage forms for temperature sensitive active materials. Such pharmaceutically active materials require, because of their sensitivity (i.e., heat inactivation and so on) particularly protective processing procedures which may be simply readily secured through the process of the present invention.

The field of use of the molded particles of the present invention is certainly not restricted to pharmaceutical purposes. Fields of utilization include biotechnology (cryoconservation of enzymes or bacteria ready nutrients in dried form), as well as in the cosmetic area (the processing of plant extract such as for example, aloe vera into tablets provides the advantage of an ideal, dry transport mode for the moisture sensitive extract and at the same time, the naturally constructed matrix system is suitable components for ointments and creams).

Because of the large number of variation and combination possibilities of the molded particles of the present invention, the release of pharmaceutically active materials may be modulated for all uses within wide parameters.

The following examples will further clarify the invention:

EXAMPLE 1

Pharmaceutical Material: Benzocaine
Prescription for the basic mass to be processed:
210 g. Gelatin (170 bloom)
50 g. Dextran (molecular weight about 10000)
29 g. Saccharose
1 g. Peppermint odorant
710 g. Distilled Water
1000 g.

The gelatin powder is mixed with peppermint odorant, the water in which the dextran as well as the saccharose is already dissolved, is added and, after pre-swelling at 50° C., the gelatin dissolves therein. Into this solution 10 g of micronized benzocaine are suspended under ultrasound agitation. Evaporation is carried out under reduced pressure, the residue is dripped into the dropping bath containing liquid nitrogen via the Cryopel ® dosing arrangement, whereby the pellets are produced. The shock frozen, round pellet-molded particles, are subjected to a primary drying in a freeze drying arrangement at −50° C. and 5 Pa (0.05 mBar) and a secondary drying at 22° C.

78% of the pellets lie in the size range of 0.8 to 1 mm. The dried pellets are directly compressed to form a chewable tablet having a mean benzocaine content of 5 mg.

EXAMPLE 2

Pharmaceutically Active Material: Potassium Chloride
Prescription for the Basic Mass to be Processed:
625 g. Collagen Hydrolysate (molecular weight 2,000–3,000 D)]
50 g. Citric Acid
2325 g. Distilled Water
3000 g.

The collagen hydrolysate and the citric acid are dissolved in water with stirring. Into this solution are added 190 g. of potassium chloride.

After defoaming in vacuum the product is dropped, via the Cryopel dosing arrangement into a dropping bath charged with liquid nitrogen whereby there are formed pellets with a mean size of 4 mm.

The water is removed by freeze drying in the method set forth in Example 1 above.

The pellets are packed in air tight bags comprising individual doses of 1 g of potassium ion. The content of the bag is readily dissolved in water at room temperature within 30 seconds.

SAMPLE 3

Pharmaceutical Material: Potassium Phenoxymethyl Penicillin
Prescription for the Basic Mass to be Worked
200 g. Dextran (molecular weight 60000)

200 g. Collagen Hydrolysate (Molecular weight 2,000–3,000)
5 g. Orange odorant
250 g. Mannitol
100 g. Saccharose
Distilled Water to 2500 g.

The components are mixed and dissolved in the water. 100 g. of potassium phenoxymethyl penicillin are dissolved in this mixture under stirring.

After defoaming in vacuum the product is dropped into a dropping bath containing liquid nitrogen to thereby form pellets. The water is subsequently removed by freeze drying.

2.31 g of the dried pellets (corresponding to a mean content of potassium phenoxymethyl penicillin of 270 mg) are sealed in individual bags and utilized as an instantly potable solution.

EXAMPLE 4

Example of matrix mass of gelatin and softener in which the pharmaceutical to be processed can be dissolved
Gelatin 150 bloom 2.6 kg
Spray dried Sorbitol 1.0 kg.
Dihydrocodeine hydrogen tadrate 0.1 kg
Water 6.3 kg The active substance is entirely dissolved in 1 kg of water with stirring. The gelatin granulate is swollen in the remaining water, dissolved at 40° C. and thereafter sorbitol and the active substance are added under stirring. After melting the gelatin and homogenizing the solution, the pellets are formed by dropping the mass into the liquid nitrogen as described in Example 1. The pellets are then dried in the usual manner at a temperature of between 20° C. and 40° C. and subsequently packed in opaque hard gelatin capsules with a mean content of 10 mg dihydrocodein tartrate. In a dissolution test (apparatus in accordance with United States Pharmacopeia XXI, 500 ml water, 37° C., 50 UpM) the amount of active material released in 4.5 minutes is 70% of the charge.

The thus obtained pellets are transparently clear and shiny.

EXAMPLE 5

Example for a matrix mass of gelatin and softening agent in which the pharmaceutical material is provided as an emulsion.
Gelatin 210 bloom 2.6 kg
Glycerin (85%) 1.25 kg
alpha-tocopherol acetate 0.25 kg
Water 6,9 kg The powdery gelatin is swollen for 40 minutes in cold water and subsequently dissolved at 50° C. Utilizing an ultrasound homogenizer the active substance is emulsified at 50° C. in the gelatin solution, The oil in water emulsion is subsequently mixed with glycerine and cryopelletized. The thus obtained pellets are dried as set forth in Example 4. The pellets which contain 25 mg of alpha-tocopherol acetate are packed in opaque hard gelatin capsules.

The thus obtained pellets are opaque, nontransparent, and shiny.

EXAMPLE 6

Example for matrix mass of gelatin and softening agent in which the active substance can be suspended.
Gelatin 250 bloom 2.5 kg
Glycerin (85%) 1.0 kg
Dexamethasone, micronized powder 0.025 kg
Water 4.0 kg The soft gelatin mass is swollen in 1 kg water and upon addition of the remaining water is dissolved at 50° C. The active substance is homogeneously distributed in this solution under stirring and subsequently the solution is mixed with the gelatin. The thus obtained suspension is cryopelletized. After conventional drying the pellets are charged to hard gelatin capsules with asteroid content of 0.5 mg.

The pellets are transparent and shiny.

EXAMPLE 7

Example for a single dosage form
Charge:
0.8 kg. Gelatin 1250 bloom
0.8 kg Spray dried Sorbitol
0.8 kg Acetyl salicylic acid
1.6 kg Water The gelatin granulate is preswollen for 30 minutes in water and thereafter dissolved at 70° C. The acetyl salicylic acid Is dispersed in the thus obtained solution and subsequently the sorbitol added thereto.

The thus produced matrix mass Is dropped into liquid nitrogen via the apparatus shown in FIG. 2 having jet set at 70° C. The shock frozen pellets are classified under cooling and have a unitary size of 8 mm.

The round molded particles are charged to a dosage dispenser and can, according to each indication, be individually dosed.

The thus produced pellets have a pleasant taste and increase their acceptability especially by during heart attack prophylaxis.

These examples are merely intended as exemplifying embodiments of the present invention. It will be clear to one skilled in the art that there are plurality of similarly several pharmaceutical, cosmetic, or other molded particles in accordance with the present invention such as powders, granulates, and generally speaking symmetrical aggregates, which were introduced or utilized within the scope of the present invention.

We claim:

1. Pharmaceutically active substance containing dried cryopellets comprising at least one active substance, the amount and activity whereof being essentially undiminished by the cryopelleting, dispersed in a matrix, at least 50% w/w whereof comprising substantially of skeleton forming water soluble hydrophilic macromolecular material selected from the group consisting of:

collagen, gelatin, fractionated gelatin, collagen hydrolysates, succinylated gelatin, plant proteins, plant protein hydrolysates, elastin hydrolysates and mixtures thereof.

2. Dried cryopellet in accordance with claim 1 characterized thereby that the hydrophilic material is a thermoreversible sol/gel former.

3. Dried cryopellet in accordance with claim 1 further comprising at least one additional skeleton forming hydrophilic material selected from the group consisting of albumin, agar agar, gum arabic, pectin, tragacanth, xanthan, natural and modified starches, dextrans, dextrins, maltodextrin, chitosan, alginates, cellulose derivatives, dextran, sugar, glycine, lactose, mannitol, polyvinyl pyrrolidone, polyacrylic acid, polymers of methacrylic acid, polymers of methacrylic acid esters and mixtures thereof said additional skeleton forming agent comprises less than 50% by weight of said matrix.

4. Dried cryopellet in accordance with claim 1 wherein said matrix further comprises a pharmaceutically acceptable inactive ingredient or carrier material.

5. Dried cryopellet in accordance with claim 1 wherein said dried cryopellet is selected from the group consisting of powders, granulates, pellets and aggregates and has substantially symmetrical dimensions.

6. Dried cryopellet in accordance with claim 1 existing as a lyophilisate.

7. Dried cryopellet in accordance with claim 1 which is rapidly dissolvable in aqueous media and wherein said matrix comprises substantially of a hydrophilic macromolecular material selected from the group consisting of plant proteins, plant protein hydrolysates, elastin hydrolysates, collagen hydrolysates, cold water soluble gelatins, succinylated gelatin, the major portion whereof having a molecular weight under $10^5$ D.

8. Dried cryopellet in accordance with claim 1 wherein said matrix additionally comprises softening agents and flavorants selected from the group consisting of:

glycerol, propylene glycol, polyethylene glycol, triacetin, sorbitol, sorbitan mixtures, glucose syrup, and mixtures thereof.

9. Dried cryopellet in accordance with claim 8 existing in solid or semisolid form.

10. Dried cryopellet in accordance with claim 2 wherein the sol/gel former is a gelatin the major portion whereof having a molecular weight above $10^5$ D.

11. Dried cryopellet in accordance with claim 1 wherein said active substance is selected from the group consisting of pharmaceutical materials of natural or synthetic origin, prophylactic materials for health care, enzymes, and microorganisms.

12. Dried cryopellet in accordance with claim 1 wherein the mode of dispersion of said active substance is solution, suspension, solid dispersion, emulsification or microemulsification.

13. Dried cryopellet in accordance with claim 1 wherein said active substance is dispersed in said matrix in the form of microcapsules or nanocapsules.

14. Dried cryopellet in accordance with claim 11 wherein said active substance is conjugated with the hydrophilic material.

15. Dried cryopellet in accordance with claim 11 wherein said matrix has a melting point range of between 35° C. and 40° C.

16. Dried cryopellet in accordance with claim 11 wherein said matrix is cross-linked with a pharmaceutically acceptable hardening material selected from the group consisting of aldoses and citral.

17. Dried cryopellet in accordance with claim 11 further comprises a hydrophilic macromolecular material as skeleton builder selected from the group consisting of alginate, alginate calcium phosphate, pectin, agar agar, cross linked poly- and methacrylic acid and succinylated gelatin.

18. Molded particle in accordance with claim 12 characterized thereby that the matrix of the molded particle is coated.

19. A pharmaceutical preparation comprising dried cryopellets of claim 1.

20. A cosmetic preparation containing dried cryopellets according to claim 1.

21. A dietetic preparation for health care comprising dried cryopellets of claim 1.

22. Mixture comprising at least one pharmaceutically active substance and a skeleton forming water soluble hydrophilic macromolecular material at least 50% w/w where of is a member selected from the group consisting of:

collagen, gelatin, fractionated gelatin, collagen hydrolysates, plant proteins, plant protein hydrolysate, elastin hydrolysate, albumin, agar agar, gum arabic, pectin, tragacanth, xanthan, natural and modified starches, dextran, dextrin, maltodextrin, chitosan, alginate, succinylated gelatin, polyvinyl alcohol, polyvinyl pyrrolidone, polyacrylic acid, polymers of methacrylic acid, polymers of methacrylic acid esters and mixtures thereof, said active substance being dispersed in said hydrophilic material.

23. Mixture in accordance with claim 22 wherein said hydrophilic material is a sol/gel former.

24. Mixture in accordance with claim 22 wherein said hydrophilic material is a thermo-reversible sol gel former derived from collagen.

25. Mixture in accordance with claim 22 further comprising an additional softening agent from 1 to 50% by weight, relative to the total mass of said hydrophilic material, selected from the group consisting of glycerol, propylene glycol, polyethylene glycol, triacetin, sorbitol, sorbitan mixture, sorbitol solution and mixtures thereof.

26. Mixture in accordance with claim 22 further comprising pharmaceutically acceptable inactive additive and carrier materials.

27. Mixture in accordance with claim 22 wherein said active substance is dissolved in, emulsified with, suspended in, microemulsified with, finely dispersed in, or conjugated with said hydrophilic material or dispersed therein in microencapsulated or nanoencapsulated form.

28. Mixture in accordance with claim 22 wherein said hydrophilic material dissolves rapidly in an aqueous medium.

29. Mixture in accordance with claim 22 wherein said hydrophilic material dissolves slowly in an aqueous medium.

30. Mixture in accordance with claim 22 wherein said hydrophilic material has a melting point in the range of about 35° C. to 40° C.

31. Mixture in accordance with claim 22 wherein said hydrophilic material is insoluble in aqueous media.

32. Mixture in accordance with claim 22 wherein sad hydrophilic material is soluble in aqueous media in a predetermined pH range.

33. Dried cryopellet in accordance with claim 11 further comprising a film coating of a hydrophilic material selected from the group consisting of poly- and methacrylic acid derivatives and cellulose derivatives.

* * * * *